(12) United States Patent
Li et al.

(10) Patent No.: US 12,201,146 B2
(45) Date of Patent: *Jan. 21, 2025

(54) ULTRASONIC ATOMIZATION CONTROL SYSTEM AND ELECTRONIC CIGARETTE

(71) Applicant: SHENZHEN FIRST UNION TECHNOLOGY CO., LTD., Shenzhen (CN)

(72) Inventors: Yonghai Li, Shenzhen (CN); Zhongli Xu, Shenzhen (CN); Huiyong Yan, Shenzhen (CN)

(73) Assignee: SHENZHEN FIRST UNION TECHNOLOGY CO., LTD., Shenzhen (CN)

( * ) Notice: Subject to any disclaimer, the term of this patent is extended or adjusted under 35 U.S.C. 154(b) by 66 days.

This patent is subject to a terminal disclaimer.

(21) Appl. No.: 18/088,653

(22) Filed: Dec. 26, 2022

(65) Prior Publication Data

US 2023/0126094 A1    Apr. 27, 2023

Related U.S. Application Data

(62) Division of application No. 15/713,737, filed on Sep. 25, 2017, now Pat. No. 11,564,414.

(30) Foreign Application Priority Data

Sep. 26, 2016   (CN) .......................... 201621082335.3

(51) Int. Cl.
*A24F 40/05* (2020.01)
*A24F 40/50* (2020.01)
(Continued)

(52) U.S. Cl.
CPC .............. *A24F 40/05* (2020.01); *A24F 40/50* (2020.01); *A61M 15/0085* (2013.01);
(Continued)

(58) Field of Classification Search
None
See application file for complete search history.

(56) References Cited

U.S. PATENT DOCUMENTS 4,113,809 A * 9/1978 Abair .................... B06B 1/0223
                                                    261/DIG. 65
5,312,281 A   5/1994 Takahashi et al.
(Continued)

FOREIGN PATENT DOCUMENTS

| CN | 105871224 A | 8/2016 | |
|---|---|---|---|
| DE | 102006054826 A1 * | 5/2008 | ............. B05B 12/00 |
| GB | 2291605 A | 1/1996 | |

OTHER PUBLICATIONS

"Machine translation of DE 102006054826," Translated Dec. 11, 2023, Espacenet.com (Year: 2023).*
European Search Report 2018.

*Primary Examiner* — Philip Y Louie
*Assistant Examiner* — Sonny V Nguyen
(74) *Attorney, Agent, or Firm* — IPRO, PLLC (57) ABSTRACT

Disclosed are an ultrasonic atomization control system and an electronic cigarette. The system includes: a current feedback circuit and/or a voltage feedback circuit, a microcontroller unit, a push-pull circuit, and an oscillator driving circuit; wherein the push-pull circuit is coupled between the microcontroller unit and the oscillator driving circuit, the current feedback circuit and/or the voltage feedback circuit are/is coupled between the oscillator driving circuit and the microcontroller unit; and the oscillator driving circuit is configured to be connected with a load; wherein the microcontroller unit is configured to output a pulse width modulation signal with a predetermined frequency and voltage to the push-pull circuit, judge a current and/or a voltage fluctuation fed back by the current feedback circuit and/or the voltage feedback circuit are/is greater than a threshold, (Continued)

and stop operation of the load if the fluctuation is greater than the threshold.

16 Claims, 5 Drawing Sheets

(51) Int. Cl.
*A61M 15/00* (2006.01)
*A61M 15/06* (2006.01)
*B05B 12/08* (2006.01)
*B05B 17/06* (2006.01)
*H02H 3/08* (2006.01)
*H02H 3/20* (2006.01)
*A24F 40/10* (2020.01)
*A61M 16/00* (2006.01)

(52) U.S. Cl.
CPC ........... *A61M 15/06* (2013.01); *B05B 12/081* (2013.01); *B05B 17/0615* (2013.01); *H02H 3/08* (2013.01); *H02H 3/20* (2013.01); *A24F 40/10* (2020.01); *A61M 2016/0024* (2013.01)

(56) References Cited

U.S. PATENT DOCUMENTS

| | | |
|---|---|---|
| 5,551,416 A | 9/1996 | Stimpson et al. |
| 5,684,406 A | 11/1997 | MacLauchlan et al. |
| 2002/0129813 A1* | 9/2002 | Litherland ........... H10N 30/802 |
| | | 128/200.16 |
| 2010/0236092 A1* | 9/2010 | Causier ................. H02H 7/537 |
| | | 34/572 |
| 2013/0063987 A1* | 3/2013 | Boku .................... H02M 3/335 |
| | | 363/21.17 |
| 2019/0037925 A1* | 2/2019 | Hon ...................... A61M 15/06 |

* cited by examiner

ULTRASONIC ATOMIZATION CONTROL SYSTEM AND ELECTRONIC CIGARETTE

CROSS-REFERENCE TO RELATED APPLICATIONS

The present disclosure claims priority to Chinese Patent Application No. 201621082335.3, filed with the Chinese Patent Office on Sep. 26, 2016, titled "ULTRASONIC ATOMIZATION CONTROL SYSTEM AND ELECTRONIC CIGARETTE", the entire contents of which are incorporated herein by reference.

TECHNICAL FIELD

The present invention relates to the field of electronics technologies, and in particular, relates to an ultrasonic atomization control system and an electronic cigarette.

BACKGROUND

An ultrasonic electronic cigarette generates ultrasonic waves by causing an atomizing sheet to resonate by using electronic electronical high-frequency oscillation, and the ultrasonic waves are propagated in tobacco liquid to cause a cavitation phenomenon, such that the tobacco liquid is atomized.

In normal cases, when the tobacco liquid is present, the current of an oscillator driving circuit substantially remains stable. However, when no tobacco liquid is present, the current of the oscillator driving circuit may be gradually increased, and the temperature of the atomizing sheet may be also gradually increased. In severe situations, the oscillator driving circuit or the atomizing sheet may be burnt.

SUMMARY

An embodiment of the present disclosure provides an ultrasonic atomization control system. The ultrasonic atomization control system includes:

a current feedback circuit and/or a voltage feedback circuit, a microcontroller unit, a push-pull circuit, and an oscillator driving circuit; wherein the push-pull circuit is coupled between the microcontroller unit and the oscillator driving circuit, the current feedback circuit and/or the voltage feedback circuit are/is coupled between the oscillator driving circuit and the microcontroller unit; and the oscillator driving circuit is configured to be connected with a load;

wherein the microcontroller unit is configured to output a pulse width modulation signal with a predetermined frequency and voltage to the push-pull circuit, judge a current and/or a voltage fluctuation fed back by the current feedback circuit and/or the voltage feedback circuit are/is greater than a threshold, and stop operation of the load if the fluctuation is greater than the threshold.

Another embodiment of the present disclosure provides an electronic cigarette.

The electronic cigarette includes an atomizing sheet and an ultrasonic atomizing control system; the control system including:

a current feedback circuit and/or a voltage feedback circuit, a microcontroller unit, a push-pull circuit, and an oscillator driving circuit; wherein the push-pull circuit is coupled between the microcontroller unit and the oscillator driving circuit, the current feedback circuit and/or the voltage feedback circuit are/is coupled between the oscillator driving circuit and the microcontroller unit; and the oscillator driving circuit is configured to be connected with the atomizing sheet;

wherein the microcontroller unit is configured to output a pulse width modulation signal with a predetermined frequency and voltage to the push-pull circuit, judge a current and/or a voltage fluctuation fed back by the current feedback circuit and/or the voltage feedback circuit are/is greater than a threshold, and stop operation of the atomizing sheet if the fluctuation is greater than the threshold.

BRIEF DESCRIPTION OF THE DRAWINGS

One or more embodiments are illustrated by way of example, and not by limitation, in the figures of the accompanying drawings, wherein elements having the same reference numeral designations represent like elements throughout. The drawings are not to scale, unless otherwise disclosed.

DETAILED DESCRIPTION

To prevent the load and circuit from being damaged by abnormal operations, the present invention provides an ultrasonic atomization control system and an electronic cigarette.

Figure 1:
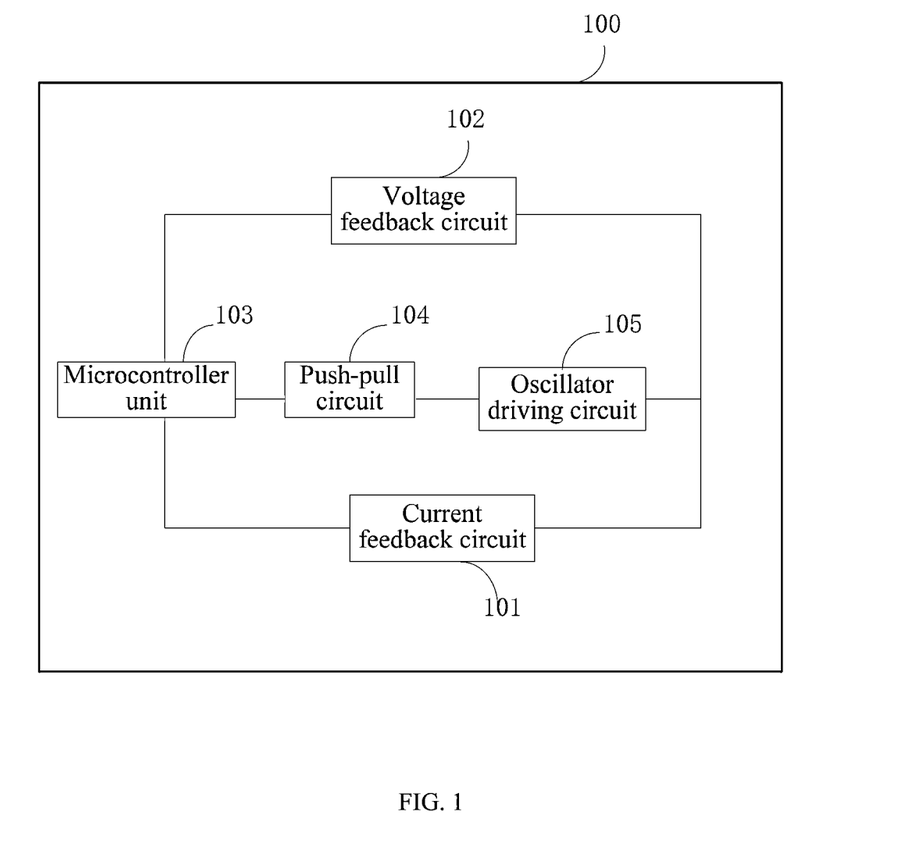
FIG. 1 is a schematic view of an ultrasonic atomization control system according to an embodiment of the present invention.

Referring to FIG. 1, FIG. 1 is a schematic view of an ultrasonic atomization control system according to an embodiment of the present invention. The ultrasonic atomization control system 100 includes a current feedback circuit 101 and/or a voltage feedback circuit 102, a microcontroller unit (MCU) 103, a push-pull circuit 104, and an oscillator driving circuit 105.

The push-pull circuit 104 is coupled between the microcontroller unit 103 and the oscillator driving circuit 105. The current feedback circuit 101 and/or the voltage feedback circuit 102 are/is coupled between the oscillator driving circuit 105 and the microcontroller unit 103. The oscillator driving circuit 105 is configured to be connected with a load. The microcontroller unit 103 is configured to output a pulse width modulation signal with a predetermined frequency to the push-pull circuit 104, judge whether a current and/or a voltage fluctuation fed back by the current feedback circuit 101 and/or the voltage feedback circuit 102 are/is greater than a threshold. If the fluctuation is greater than the threshold, the microcontroller unit 103 turns off the oscillator driving circuit 105, that is, stops operation of the load.

Figure 2:
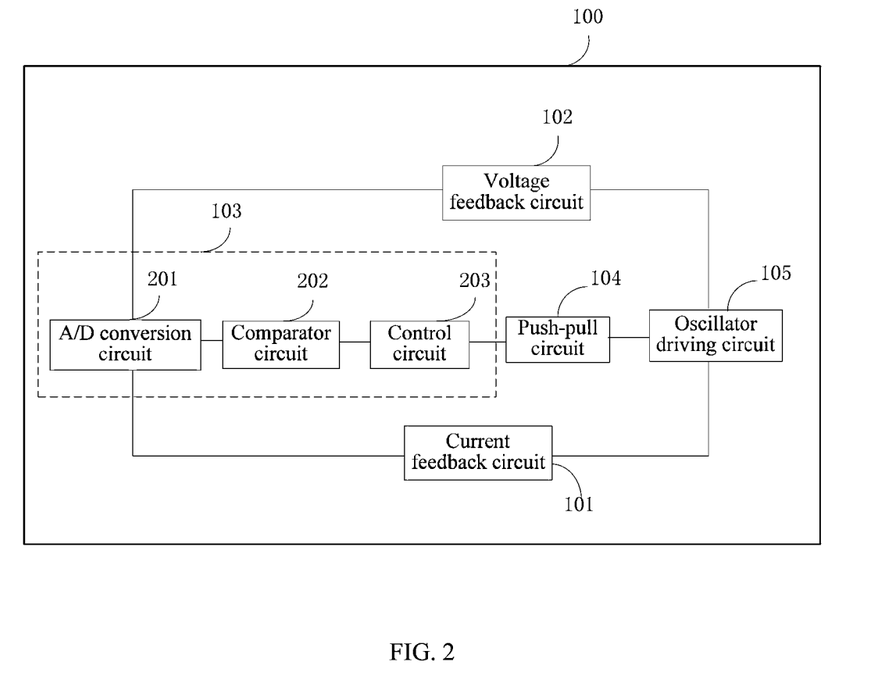
FIG. 2 is a schematic view of details of the ultrasonic atomization control system shown in FIG. 1.

Referring to FIG. 2, FIG. 2 is a schematic view of details of the ultrasonic atomization control system 100. The microcontroller unit 103 includes an A/D conversion circuit 201, a comparator circuit 202 and a control circuit 203.

An input end of the A/D conversion circuit 201 is coupled with an output end of the current feedback circuit 101 and/or the voltage feedback circuit 102. The A/D conversion circuit 201 is configured to convert a feedback current signal and/or a feedback voltage signal into a digital signal and input the digital signal to the comparator circuit 202.

The comparator circuit 202 is coupled between the A/D conversion circuit 201 and the control circuit 203. The comparator circuit 202 is configured to compare the digital signal received from the A/D conversion circuit 201 with the threshold. If the digital signal is greater than the threshold, The comparator circuit 202 inputs a first signal to the control circuit 203.

An output end of the control circuit 203 is coupled with an output end of the push-pull circuit 104. The control circuit 203 is configured to output a pulse width modulation signal to the push-pull circuit 104. When the control circuit 203 receives the first signal, the control circuit 203 controls the output pulse width modulation signal to be in a low level state, and thus controls the load connected with the oscillator driving circuit 105 to stop operating.

Figure 3:
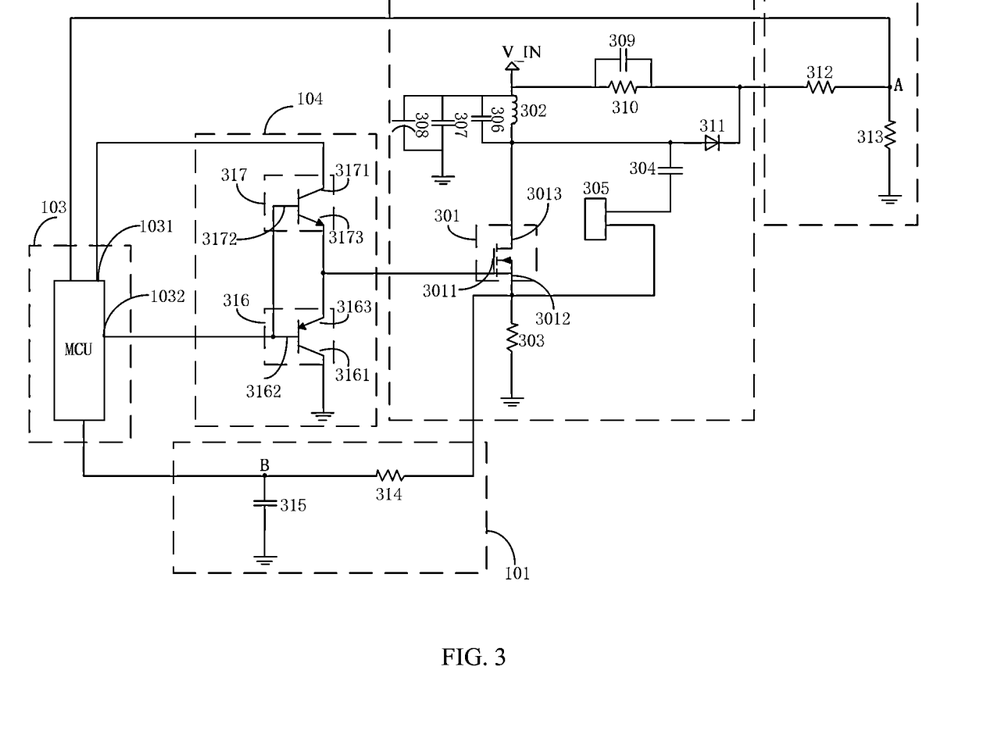
FIG. 3 is a schematic view of an exemplary circuit of the ultrasonic atomization control system shown in FIG. 1.

Referring to FIG. 3, to practice the above scheme, the present invention schematically provides a circuit view of an ultrasonic atomization control system.

The oscillator driving circuit 105 includes a control switch 301 and an inductor 302. The control switch 301 includes a control end 3011, a first end 3012 and a second end 3013. The control end 3011 is connected with the push-pull circuit 104, the first end 3012 is connected with a first grounding resistor 303, and the second end 3013 is connected with the load 305 through a first capacitor 304. A first end 3012 of the control switch 301 is also connected with the load 305. The load 305 may be an oscillator, an atomizing sheet or both, and the type of the load 305 is not limited herein. One end of the inductor 302 is connected with the second end 3013 of the control switch 301, and the other end of the inductor 302 is connected with a voltage source. The voltage source may be 24 V or 12 V or the like, which is not limited herein.

The oscillator driving circuit 105 further includes a second capacitor 306, a third capacitor 307 and a fourth capacitor 308. The second capacitor 306 is connected in parallel with the two ends of the inductor 302. The third capacitor 307, and the fourth capacitor 308 and the inductor 302 are connected in parallel. One ends of the third capacitor 307 and the fourth capacitor 308 are connected with one end of the inductor 302, which is connected with the voltage source. The other ends of the third capacitor 307 and the fourth capacitor 308 are connected to ground. The circuit formed by the above three capacitors is configured to reduce electromagnetic radiation to users.

The oscillator driving circuit 105 further includes a fifth capacitor 309 and a first resistor 310 that are connected in parallel, and a diode 311. A positive end of the diode 311 is connected with the first capacitor 304, and a negative end of the diode 311 is connected with one ends of the fifth capacitor 309 and the first resistor 310 that are connected in parallel. The other ends of the fifth capacitor 309 and the first resistor 310 that are connected in parallel are connected with one end of the inductor 302, which is connected with the voltage source.

The voltage feedback circuit 102 includes a second resistor 312 and a third resistor 313. The second resistor 312 is connected in series between the negative end of the diode 311 and the microcontroller unit 103. One end of the third resistor 313 is connected between the second resistor 312 and the microcontroller unit 103, wherein the third resistor 313 is a grounding resistor. A connection point A between the second resistor 312 and the third resistor 313 is configured as a voltage feedback point and is coupled with the microcontroller unit 103. In other embodiments, the second resistor 312 may also be disposed between the positive end of the diode 311 and the first capacitor 304.

The current feedback circuit 101 includes a fourth resistor 314 and a sixth capacitor 315. The fourth resistor 314 is coupled between the first end 3012 of the control switch 301 and the microcontroller unit 103, wherein the sixth capacitor 315 is a grounding capacitor. A connection point B between the fourth resistor 314 and the sixth capacitor 315 is configured as a current feedback point and is coupled with the microcontroller unit 103. In other embodiments, the current feedback point may also be a connection point between the control switch 301 and the load 305, that is, the fourth resistor 314 and the sixth capacitor 315 are not needed.

The push-pull circuit 104 includes a first triode 316 and a second triode 317. The first triode 316 includes a first collector 3161, a first base 3162 and a first emitter 3163, and the second triode 317 includes a second collector 3171, a second base 3172 and a second emitter 3173. The second collector 3171 is coupled with a first output end 1031 of the microcontroller unit 103, the second base 3172 is connected with the first base 3162 and is coupled with a second output end 1032 of the microcontroller unit 103, the second emitter 3173 is connected with the first emitter 3163 and is coupled with the control end 3011 of the control switch 301, and wherein the first collector 3161 is connected to ground. In the embodiment, the first output end 1031 of the microcontroller unit 103 is a power output end, and the second output end 1032 of the microcontroller unit 103 is a pulse width modulation signal output end. The push-pull circuit 104 is configured to amplify an input pulse width modulation signal.

In some exemplary embodiments, when the load 305 at the oscillator driving circuit 105 is in an abnormal operation state, if it is detected that a fluctuation range of the feedback current or the feedback voltage exceeds the threshold, the microcontroller unit 103 controls the output pulse width modulation signal to be in a low level state, such that the control switch 301 of the oscillator driving circuit 105 is turned off, and thus the load 305 stops operating.

In an application scenario, the threshold is defined as +30%, and in other application scenarios, the threshold may be defined as other values, which is not limited in the present invention.

Figure 4:
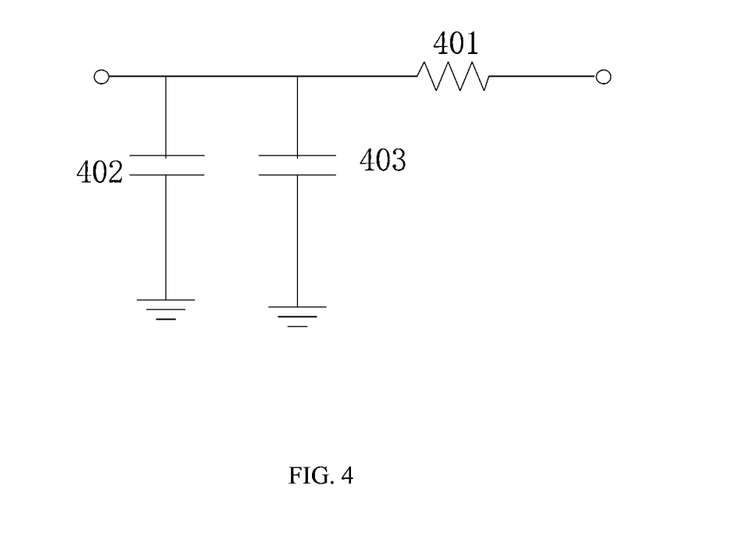
FIG. 4 is a schematic view of a filter circuit of the ultrasonic atomization control system according to an embodiment of the present invention.
Figure 5:
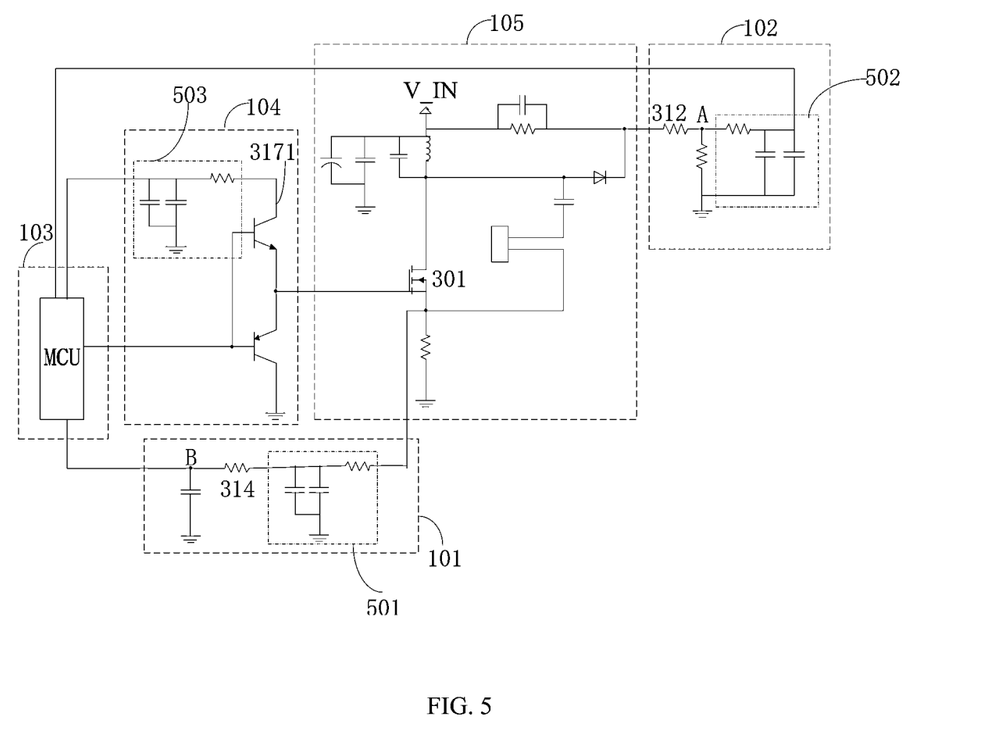
FIG. 5 is a schematic view of an exemplary circuit of an ultrasonic atomization control system having the filter circuit shown in FIG. 4 according to an embodiment of the present invention.

Referring to FIG. 4 and FIG. 5, in an application environment, an ultrasonic atomization control system further includes a filter circuit. FIG. 4 is a schematic view of a filter circuit according to an embodiment of the present invention. The filter circuit is of a typical x-shaped structure. The filter circuit includes a resistor 401 and two grounding capacitors 402 and 403 that are connected in parallel between two ends of the resistor 401, and the filter circuit is coupled with the ultrasonic atomization control system 100 through the resistor 401. In other embodiments, the filter circuit may be of an L-shaped structure, a T-shaped structure or the like structure.

As illustrated in FIG. 5, FIG. 5 is a schematic view of an exemplary circuit of an ultrasonic atomization control system having the filter circuit in FIG. 4 according to an embodiment of the present invention.

The current feedback circuit 101 further includes a first filter circuit 501 coupled between the control switch 301 and the microcontroller unit 103. The specific position of the first filter circuit 501 is not limited in this embodiment. In an exemplary embodiment, the first filter circuit 501 may be coupled between the control switch 301 and the fourth resistor 314, or may be coupled between the fourth resistor 314 and the microcontroller 103.

The voltage feedback circuit 102 further includes a second filter circuit 502 coupled between the oscillator driving circuit 105 and the microcontroller unit 103. The specific position of the second filter circuit 502 is not limited in this embodiment. In an exemplary embodiment, the second filter circuit 502 may be coupled between the voltage feedback point A and the microcontroller unit 103, or may be coupled between the voltage feedback point A and the second resistor 312.

The push-pull circuit 104 further includes a third filter circuit 503 coupled between the microcontroller unit 103 and the second collector 3171.

Figure 6:
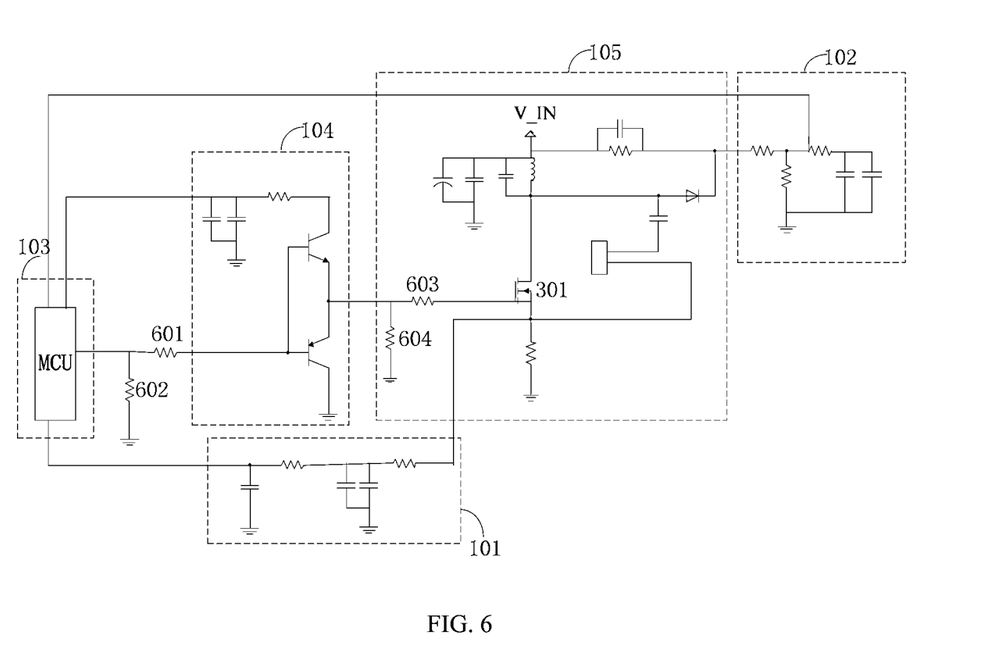
FIG. 6 is a schematic view of an exemplary circuit of an ultrasonic atomization control system according to an embodiment of the present invention.

To ensure secure operation of the ultrasonic atomization control system 100, some resistors or capacitors may also be connected in the circuit of the ultrasonic atomization control system 100. Referring to FIG. 6, FIG. 6 is a schematic view of an exemplary circuit of an ultrasonic atomization control system according to an embodiment of the present invention. A resistor 601 and a grounding resistor 602 that are connected in parallel are connected between the push-pull circuit 104 and the microcontroller unit 103. A resistor 603 and a grounding resistor 604 that are connected in parallel are connected between the push-pull circuit 104 and the oscillator driving circuit 105. In other embodiments, the position, type and number of connected resistors may be different, and the connected resistor may also be a capacitor.

Figure 7:
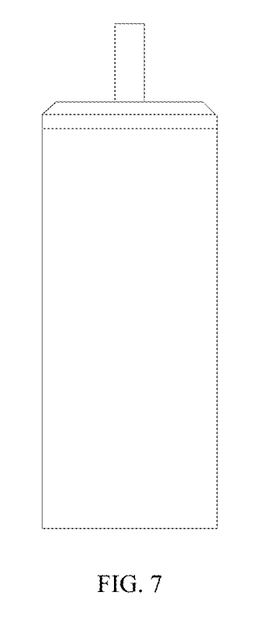
FIG. 7 is a schematic structural view of an electronic cigarette according to an embodiment of the present invention.
Figure 8:
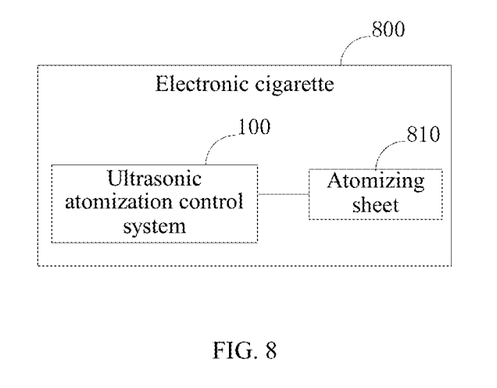
FIG. 8 is a schematic block diagram of the electronic cigarette shown in FIG. 7.

Referring to FIG. 7 and FIG. 8, FIG. 7 is a schematic structural view of an electronic cigarette according to an embodiment of the present invention, and FIG. 8 is a schematic block diagram of the electronic cigarette shown in FIG. 7. The electronic cigarette 800 includes an atomizing sheet 810 and the ultrasonic atomization control system 100 as described in any of the above embodiments. When the electronic cigarette 800 receives an operation start instruction, the microcontroller unit therein outputs a pulse width modulation signal with a specific frequency and voltage to the push-pull circuit. While the electronic cigarette 800 is operating, the microcontroller unit detects in real time a feedback current or a feedback voltage of the oscillator driving circuit. When it is detected that the feedback current or the feedback voltage exceeds a threshold, the pulse width modulation signal output by the microcontroller unit is in a low level state, such that the control switch of the oscillator driving circuit is turned off, and thus the atomizing sheet stops operating, thereby preventing the atomizing sheet and the ultrasonic atomization control system 100 from being damaged.

Described above are exemplary embodiments of the present invention, but are not intended to limit the scope of the present invention. Any equivalent structure or equivalent process variation made based on the specification and drawings of the present invention, which is directly or indirectly applied in other related technical fields, fall within the scope of the present invention.

What is claimed is:

1. An ultrasonic atomization control system, comprising: a current feedback circuit and a voltage feedback circuit, a microcontroller unit, a push-pull circuit, and an oscillator driving circuit; wherein the push-pull circuit is coupled between the microcontroller unit and the oscillator driving circuit, the current feedback circuit is coupled between the oscillator driving circuit and the microcontroller unit, the voltage feedback circuit is coupled between the oscillator driving circuit and the microcontroller unit; and the oscillator driving circuit is configured to be connected with a load;

wherein the microcontroller unit is configured to output a pulse width modulation signal with a predetermined frequency and voltage to the push-pull circuit, and stop operation of the load, based on the current fluctuation fed back by the current feedback circuit and the voltage fluctuation fed back by the voltage feedback circuit;

wherein the oscillator driving circuit comprises:

a control switch, the control switch comprising a control end, a first end and a second end, wherein the control end of the control switch is directly connected with the push-pull circuit, the first end of the control switch is directly connected with a first grounding resistor, the second end of the control switch is connected with the load through a first capacitor, and the first end of the control switch is further directly connected with the load;

an inductor having a first connecting end and a second connecting end, the first connecting end of the inductor being directly connected with the second end of the control switch, and the second connecting end of the inductor being directly connected with a voltage source;

a fifth capacitor and a first resistor that are directly connected in parallel, and a diode;

wherein a positive end of the diode is directly connected with the first capacitor and the second end of the control switch, a negative end of the diode is directly connected with one of the ends of the fifth capacitor and the first resistor that are directly connected in parallel; and the other end of the fifth capacitor and the first resistor is directly connected in parallel are directly connected with the second connecting end of the inductor.

2. The control system according to claim 1, wherein the microcontroller unit is configured to judge whether or not a current fluctuation fed back by the current feedback circuit is greater than a first threshold, and whether or not a voltage fluctuation fed back by the voltage feedback circuit is greater than a second threshold, and stop operation of the load if the current fluctuation is greater than the first threshold or stop operation of the load if the voltage fluctuation is greater than the second threshold.

3. The control system according to claim 1, wherein the oscillator driving circuit further comprises: a second capacitor, a third capacitor and a fourth capacitor; wherein the second capacitor is connected in parallel with the first connecting end and the second connecting end of the inductor; the third capacitor and the fourth capacitor are connected in parallel with the inductor, one of the ends of the third capacitor and the fourth capacitor being connected with the second connecting end of the inductor; and wherein the third capacitor and the fourth capacitor are both grounding capacitors.

4. The control system according to claim 1, wherein the voltage feedback circuit comprises: a second resistor and a third resistor that are connected in series; wherein one of the ends of the second resistor and the third resistor that are connected in series are connected with the negative end of the diode, the third resistor is a grounding resistor, and wherein a connection point between the second resistor and the third resistor is configured as a voltage feedback point and is connected with the microcontroller unit.

5. The control system according to claim 4, wherein the voltage feedback circuit further comprises a second filter circuit coupled between the second resistor and the microcontroller unit.

6. The control system according to claim 1, wherein the current feedback circuit comprises: a fourth resistor and a sixth capacitor that are connected in series; wherein
one end of the fourth resistor is connected with the first end of the control switch, the sixth capacitor is a grounding capacitor, and wherein a connection point between the fourth resistor and the sixth capacitor is configured as a current feedback point and is connected with the microcontroller unit.

7. The control system according to claim 6, wherein the current feedback circuit further comprises a first filter circuit coupled between the fourth resistor and the control switch.

8. The control system according to claim 6, wherein the current feedback circuit further comprises a first filter circuit coupled between the fourth resistor and the microcontroller unit.

9. The control system according to claim 1, wherein the push-pull circuit comprises: a first triode and a second triode; wherein
the first triode comprises a first collector, a first base and a first emitter, and the second triode comprises a second collector, a second base and a second emitter; wherein the second collector is coupled with a first output end, the second base is connected with the first base and coupled with a second output end, the second emitter is connected with the first emitter and coupled with the control end of the control switch, and wherein the first collector is connected to ground;
wherein the first output end is a power end, and the second output end is a pulse width modulation signal output end of the microcontroller unit.

10. The control system according to claim 1, further comprising a filter circuit; wherein
the filter circuit comprises a resistor and two grounding capacitors that are connected in parallel between two ends of the resistor, and the filter circuit is coupled with the ultrasonic atomization control system through the resistor.

11. An electronic cigarette, comprising an atomizing sheet which is a load and an ultrasonic atomizing control system; wherein
the ultrasonic atomization control system comprises:
a current feedback circuit and a voltage feedback circuit, a microcontroller unit, a push-pull circuit, and an oscillator driving circuit;
wherein the push-pull circuit is coupled between the microcontroller unit and the oscillator driving circuit, the current feedback circuit and the voltage feedback circuit are coupled between the oscillator driving circuit and the microcontroller unit; and the oscillator driving circuit is configured to be connected with the load;
wherein the microcontroller unit is configured to output a pulse width modulation signal with a predetermined frequency and voltage to the push-pull circuit, and stop operation of the load, based on the current fluctuation fed back by the current feedback circuit and the voltage fluctuation fed back by the voltage feedback circuit;
wherein the oscillator driving circuit comprises:
a control switch, the control switch comprising a control end, a first end and a second end, wherein the control end of the control switch is directly connected with the push-pull circuit, the first end of the control switch is directly connected with a first grounding resistor, the second end of the control switch is directly connected with the load through a first capacitor, and the first end of the control switch is further directly connected with the load;
an inductor having a first connecting end and a second connecting end, the first connecting end of the inductor being directly connected with the second end of the control switch, and the second connecting end of the inductor being directly connected with a voltage source;
a fifth capacitor and a first resistor that are directly connected in parallel, and a diode:
wherein a positive end of the diode is directly connected with the first capacitor and the second end of the control switch, a negative end of the diode is directly connected with one of the ends of the fifth capacitor and the first resistor that are directly connected in parallel; and the other end of the fifth capacitor and the first resistor is that are directly connected in parallel are directly connected with the second connecting end of the inductor.

12. The electronic cigarette according to claim 11, wherein the oscillator driving circuit further comprises: a second capacitor, a third capacitor and a fourth capacitor; wherein
the second capacitor is connected in parallel with the the first connecting end and the second connecting end of the inductor; the third capacitor and the fourth capacitor are connected in parallel with the inductor, one of the ends of the third capacitor and the fourth capacitor being connected with the second connecting end of the inductor; and wherein the third capacitor and the fourth capacitor are both grounding capacitors.

13. The electronic cigarette according to claim 11, wherein the voltage feedback circuit comprises: a second resistor and a third resistor that are connected in series; wherein
one of the ends of the second resistor and the third resistor and the third resistor that are connected in series are connected with the negative end of the diode, the third resistor is a grounding resistor, and wherein a connection point between the second resistor and the third resistor is configured as a voltage feedback point and is connected with the microcontroller unit.

14. The electronic cigarette according to claim 11, wherein the current feedback circuit comprises: a fourth resistor and a sixth capacitor that are connected in series; wherein
one end of the fourth resistor is connected with the first end of the control switch, the sixth capacitor is a grounding capacitor, and wherein a connection point between the fourth resistor and the sixth capacitor is configured as a current feedback point and is connected with the microcontroller unit.

15. The electronic cigarette according to claim 11, wherein the push-pull circuit comprises: a first triode and a second triode; wherein the first triode comprises a first collector, a first base and a first emitter, and the second triode comprises a second collector, a second base and a second emitter; wherein the second collector is coupled with a first output end, the second base is connected with the first base and coupled with a second output end, the second emitter is connected with the first emitter and coupled with the control end of the control switch, and wherein the first collector is connected to ground;

wherein the first output end is a power end, and the second output end is a pulse width modulation signal output end of the microcontroller unit.

16. The electronic cigarette according to claim 11, further comprising a filter circuit;

wherein the filter circuit comprises a resistor and two grounding capacitors that are connected in parallel between two ends of the resistor, and the filter circuit is coupled with the ultrasonic atomization control system through the resistor.

* * * * *